US006965812B2

(12) United States Patent
Wang et al.

(10) Patent No.: US 6,965,812 B2
(45) Date of Patent: Nov. 15, 2005

(54) SPEECH INTERFACE FOR AN AUTOMATED ENDOSCOPIC SYSTEM

(75) Inventors: Yulun Wang, Goleta, CA (US); Darrin Uecker, Santa Barbara, CA (US)

(73) Assignee: Computer Motion, Inc., Sunnyvale, CA (US)

( * ) Notice: Subject to any disclaimer, the term of this patent is extended or adjusted under 35 U.S.C. 154(b) by 402 days.

(21) Appl. No.: 10/095,488

(22) Filed: Mar. 11, 2002

(65) Prior Publication Data

US 2002/0183894 A1 Dec. 5, 2002

Related U.S. Application Data

(63) Continuation of application No. 08/310,665, filed on Sep. 22, 1994, now Pat. No. 6,463,361.

(51) Int. Cl.⁷ ........................ G05B 15/00; G05B 19/10; G06F 19/00
(52) U.S. Cl. ........................ 700/258; 700/245; 318/567
(58) Field of Search ................................. 700/258, 245; 318/567

(56) References Cited

U.S. PATENT DOCUMENTS

| 977,825 | A | 12/1910 | Murphy |
| 3,171,549 | A | 3/1965 | Orloff |
| 3,280,991 | A | 10/1966 | Melton et al. |
| 4,058,001 | A | 11/1977 | Waxman |
| 4,128,880 | A | 12/1978 | Cray, Jr. |
| 4,221,997 | A | 9/1980 | Flemming |
| 4,367,998 | A | 1/1983 | Causer |
| 4,401,852 | A | 8/1983 | Noso et al. |
| 4,456,961 | A | 6/1984 | Price et al. |
| 4,460,302 | A | 7/1984 | Moreau et al. |
| 4,474,174 | A | 10/1984 | Petruzzi |
| 4,491,135 | A | 1/1985 | Klein |
| 4,503,854 | A | 3/1985 | Jako |
| 4,517,963 | A | 5/1985 | Michel |

(Continued)

FOREIGN PATENT DOCUMENTS

| DE | U 9204118.3 | 7/1992 |
| DE | 4310842 C2 | 1/1995 |
| EP | 0239409 A1 | 9/1987 |
| EP | 0424687 A1 | 5/1991 |
| EP | 0776738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

"Endocorporeal Surgery Using Remote Manipulators" (Ned S. Rasor and J.W. Spickler) Remotely Manned Systems—Exploration and Operation in Space, California Institute of Technology 1973.

(Continued)

*Primary Examiner*—George B. Davis
(74) *Attorney, Agent, or Firm*—Townsend and Townsend and Crew LLP; Mark D. Barrish, Esq.

(57) ABSTRACT

A robotic system which controls the movement of a surgical instrument in response to voice commands from the user. The robotic system has a computer controlled arm that holds the surgical instrument. The user provides voice commands to the computer through a microphone. The computer contains a phrase recognizer that matches the user' speech with words stored in the computer. Matched words are then processed to determine whether the user has spoken a robot command. If the user has spoken a recognized robot command the computer will move the robotic arm in accordance with the command.

33 Claims, 3 Drawing Sheets

U.S. PATENT DOCUMENTS

| | | |
|---|---|---|
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Andersson et al. |
| 4,815,450 A | 3/1989 | Patel |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,436,542 A * | 7/1995 | Petelin et al. ................ 318/567 |
| 5,442,728 A | 8/1995 | Kaufman et al. |
| 5,443,484 A | 8/1995 | Kirsch et al. |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,458,574 A | 10/1995 | Machold et al. |
| 5,476,010 A | 12/1995 | Fleming et al. |
| 5,490,117 A | 2/1996 | Oda et al. |
| 5,490,843 A | 2/1996 | Hildwein et al. |
| 5,506,912 A | 4/1996 | Nagasaki et al. |
| 5,512,919 A | 4/1996 | Araki |
| 5,515,478 A | 5/1996 | Wang |
| 5,553,198 A | 9/1996 | Wang et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,657,429 A | 8/1997 | Wang et al. |
| 5,658,250 A | 8/1997 | Blomquist et al. |
| 5,695,500 A | 12/1997 | Taylor et al. |
| 5,696,837 A | 12/1997 | Green |
| 5,735,290 A | 4/1998 | Sterman et al. |
| 5,749,362 A | 5/1998 | Funda et al. |
| 5,754,741 A | 5/1998 | Wang et al. |
| 5,776,126 A | 7/1998 | Wilk et al. |
| 5,779,623 A | 7/1998 | Bonnell |
| 5,800,423 A | 9/1998 | Jensen |
| 5,807,284 A | 9/1998 | Foxlin |
| 5,808,665 A | 9/1998 | Green |
| 5,813,813 A | 9/1998 | Daum et al. |
| 5,817,084 A | 10/1998 | Jensen |
| 5,859,934 A | 1/1999 | Green |
| 5,878,193 A | 3/1999 | Wang et al. |

| | | |
|---|---|---|
| 5,931,832 A | 8/1999 | Jensen |
| 5,950,629 A | 9/1999 | Taylor et al. |
| 6,024,695 A | 2/2000 | Taylor et al. |
| 6,201,984 B1 | 3/2001 | Funda et al. ................ 600/407 |

OTHER PUBLICATIONS

"A Survey Study of Teleoperators, Robotics, and Remote Systems Technology" (Arthur D. Alexander, III) Remotely Manned Systems—Exploration and Operation in Space, California Institute of Technology 1973.

"Impacts of Telemation on Modern Society" (Arthur D. Alexander, III), On the Theory and Practice of Robots and Manipulators vol. II, 1974.

Transcript of a video presented by SRI at the 3rd World Congress of Endoscropic Surgery in Bordeaux on Jun. 18–20, 1992, in Washington on Apr. 9, 1992, and in San Diego, CA on Jun. 4–7, 1992, entitled "Telepresence Surgery—The Future of Minimally Invasive Medicine".

Statutory Declaration of Dr. Philip S. Green, presenter of the video entitled "Telepresence Surgery—The Future of Minimally Invasive Medicine".

Abstract of a presentation "Telepresence: Advanced Teleoperator Technology for Minimally Invasive Surgery" (P. Green et al.) given at the 3rd World Congress of Endoscopic Surgery in Bordeaux, Jun. 18–20, 1992.

Abstract of a presentation "Telepresence: Advanced Teleoperator Technology for Minimally Invasive Surgery", (P. Green et al.) given at "Medicine meets virtual reality" symposium in San Diego, Jun. 4–7, 1992.

Abstract of a presentation "Camera Control for Laparoscopic Surgery by Speech–Recognizing Robot: Constant Attention and Better Use of Personnel" (Colin Besant et al.) given at the 3rd World Congress of Endoscopic Surgery in Bordeaux, Jun. 18–20, 1992.

"A Literature Review: Robots in Medicine" (B. Preising et al.) IEEE Jun. 1991.

"Robots for the Operating Room" (Elizabeth Corcoran), The New York Times, Sunday Jul. 19, 1992, Section 3, p. 9, col. 1.

"Taming the Bull: Safety in a Precise Surgical Robot" (Russell H. Taylor et al.), IEEE 1991.

Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18–20, 1992.

Abstract of a presentation "3–D Vision Technology Applied to Advanced Minimally Invasive Surgery Systems" given at the 3rd World Congress of Endoscopic Surgery in Bordeaux, Jun. 18–20, 1992.

"Analysis of the Surgeon's Grasp for Telerobotic Surgical Manipulation" (Frank Tendick and Lawrence Stark), IEEE 1989.

"Kinematic Control and Visual Display of Redundant Teleoperators" (Hardi Das et al.), IEEE 1989.

"A New System for Computer Assisted Neurosurgery" (S. Lavallee), IEEE 1989.

"An Advanced Control Micromanipulator for Surgical Applications" (Ben Gayed et al.), Systems Science vol. 13 1987.

"Force Feedback–Based Telemicromanipulation for Robot Surgery on Soft Tissues" (A.M. Sabatini et al.), IEEE 1989.

"Six–Axis Bilateral Control of an Articulated Slave Manipulator Using a Cartesian Master Manipulator" (Masao Inoue), Advanced Robotics 1990.

"On a Micro–Manipulator for Medical Application—Stability Consideration of its Bilateral Controller" (S. Majima et al.), Mechatronics 1991.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon–Machine Interface for Teleoperated Microsurgery" (Steve Charles M.D. et al.), IEEE 1989.

"A Robot in an Operating Room: A Bull in a China Shop" (J.M. Dolan et al.), IEEE 1987.

Abstract of a presentation "Concept and Experimental Application of a Surgical Robotic System the Steerable MIS Instrument SMI" given at the 3rd World Congress of Endoscopic Surgery in Bordeaux, Jun. 18–20, 1992.

Abstract of a presentation given at the 3rd World Congress of Endoscopic Surgery in Bordeaux, Jun. 18–20, 1992, entitled "Session 15/1".

Abstract of a presentation "A Pneumatic Controlled Sewing Device for Endoscopic Application the MIS Sewing Instrument MSI" given at the 3rd World Congress of Endoscopic Surgery in Bordeaux, Jun. 18–20, 1992.

Abstract of a presentation given at the 3rd World Congress of Endoscopic Surgery in Bordeaux (Jun. 18 to 20, 1992), entitled "Session 15/2".

Abstract of a presentation given at the 3rd World Congress of Endoscopic Surgery in Bordeaux (Jun. 18 to 20, 1992), entitled Session 15/4.

Abstract of a presentation given at the 3rd World Congress of Endoscopic Surgery in Bordeaux (Jun. 18 to 20, 1992), entitled "Session 15/5".

"Properties of Master–Slave Robots" (C. Vibet), Motor–con 1987.

"A New Microsurgical Robot System for Corneal Transplantation" (Noriyuki Tejima), Precision Machinery 1988.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis" (H. Kazerooni), IEEE 1989.

"Power and Impedance Scaling in Bilateral Manipulation" (J. Edward Colgate), IEEE 1991.

"S.M.O.S.: Stereotaxical Microtelemanipulator for Ocular Surgery" (Aicha Guerrouad and Pierre Vidal), IEEE 1989.

"Motion Control for a Sheep Shearing Robot" (James P. Trevelyan et al.), Proceedings of the 1st International Symposium on Robotics Research, MIT, Cambridge, Massachusetts, USA, 1983.

"Robots and Telechirs" (M.W. Thring), Wiley 1983.

Industrial Robotics (Gordon M. Mair), Prentice Hall 1988 (pp. 41–43, 49–50, 54, 203–209 enclosed).

"Student Reference Manual for Electronic Instrumentation Laboratories" (Wolf et al.), Prentice Hall, New Jersey 1990, pp. 498 and 499.

* cited by examiner

SPEECH INTERFACE FOR AN AUTOMATED ENDOSCOPIC SYSTEM

This application is a continuation of application Ser. No. 08/310,665 filed Sep. 22, 1994, now U.S. Pat. No. 6,463, 361.

BACKGROUND OF THE INVENTION

1. Field of the Invention

The present invention relates to a robotic system that moves a surgical instrument in response to voice commands from the user.

2. Description of Related Art

To reduce the invasiveness of surgery, endoscopes are commonly utilized to view the internal organs of a patient. One end of the endoscope contains a lens which is inserted into the patient through a small incision in the skin. The lens focuses an image that is transmitted by fiber optic cable to a camera located at the opposite end of the endoscope. The camera is coupled to a monitor that displays the image of the patient.

The endoscope can be used in conjunction with another surgical instrument that is inserted into the patient. An assistant typically hold the endoscope while the surgeon manipulates the surgical instrument. The assistant moves the endoscope in response to instructions from the surgeon. Any miscommunication between the surgeon and the assistant may result in an error in the movement of the endoscope, thereby requiring the surgeon to repeat the instruction. Additionally, holding the endoscope for a significant amount of time may cause the assistant to become fatigued.

U.S. application Ser. No. 07/927,801 discloses a robotic arm that holds and moves an endoscope. The surgeon can move the robotic arm by depressing a foot pedal. The foot pedal is connected to a computer which moves the arm and the scope. Although the '801 system effectively moves the endoscope, the surgeon must continually manipulate the foot pedal, a process which may detract from the surgical procedure. It would be desirable to provide a robotic endoscopic system that can be controlled by voice commands from the user.

SUMMARY OF THE INVENTION

The present invention is a robotic system which controls the movement of a surgical instrument in response to voice commands from the user. The robotic system has a computer controlled arm that holds the surgical instrument. The user provides voice commands to the computer through a microphone. The computer contains a phrase recognizer that matches the user's speech with words stored in the computer. Matched words are then processed to determine whether the user has spoken a robot command. If the user has spoken a recognized robot command the computer will move the robotic arm in accordance with the command.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
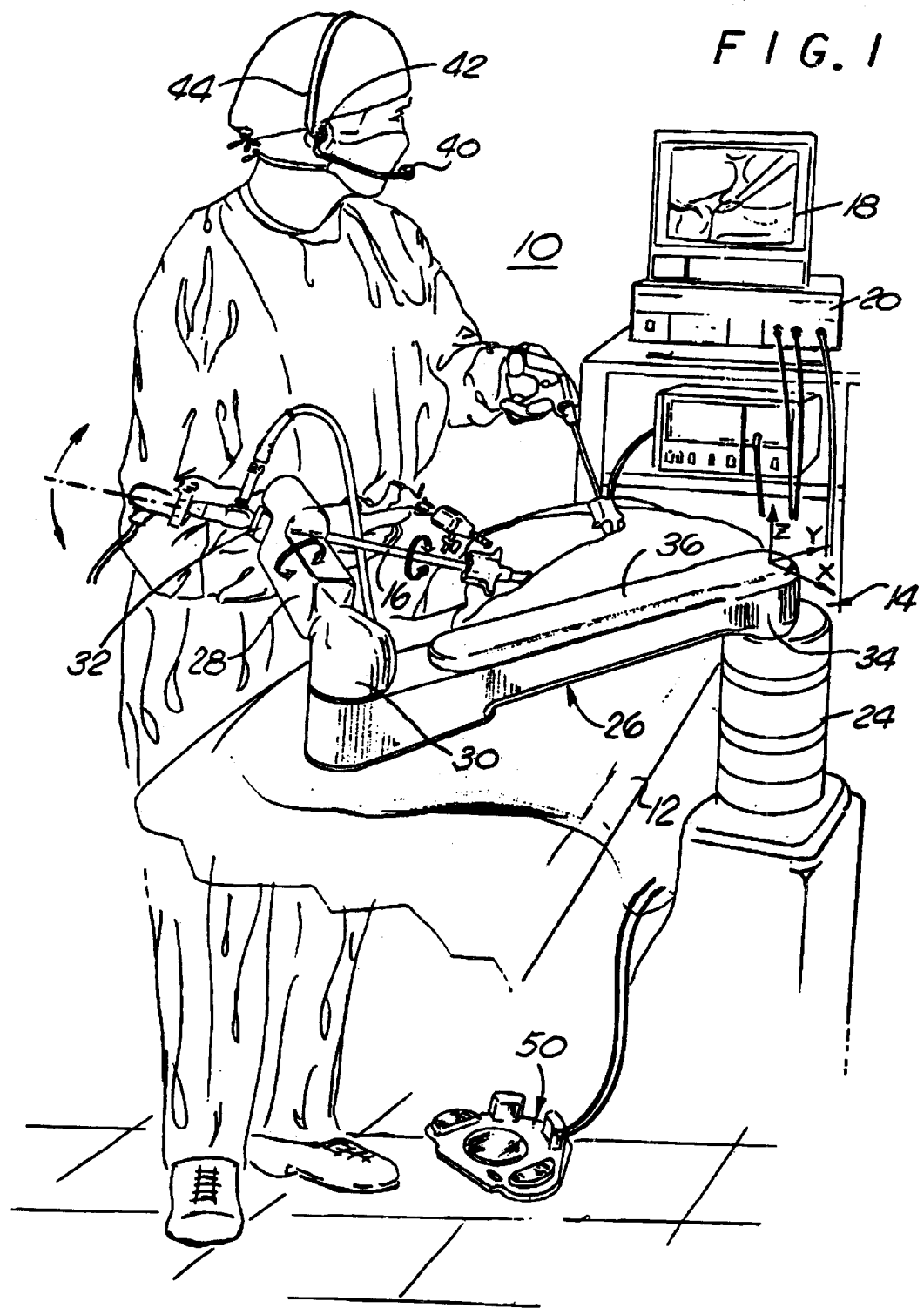
FIG. 1 is a perspective view of a robotic endoscope system of the present invention.

Referring to the drawings more particularly by reference numbers, FIG. 1 shows a robotic system 10 of the present invention. The system 10 is typically used in a sterile operating room where a surgeon performs a surgical procedure on a patient. The patient is placed on a operating table 12. Attached to the table 12 is a robotic arm assembly 14 which can move a surgical instrument 16 relative to the table 12 and the patient. The surgical instrument 16 is typically an endoscope which is inserted into the abdomen of the patient 12. The endoscope 16 enters the patient through a cannula, wherein the scope 16 rotate about a cannula pivot point. The endoscope is typically connected to a monitor 18 which allows the surgeon to view the organs, etc. of the patient. Although an endoscope is described and shown, it is to be understood that the present invention can be used with other surgical instruments.

The robotic arm assembly 14 controlled by a computer 20. In the preferred embodiment, the robotic arm assembly 16 includes a linear actuator 24 fixed to the table 14. The linear actuator 24 is connected to a linkage arm assembly 26 and adapted to move the linkage assembly 26 along the z axis of a first coordinate system. The first coordinate system also has an x axis and a y axis.

Figure 2:
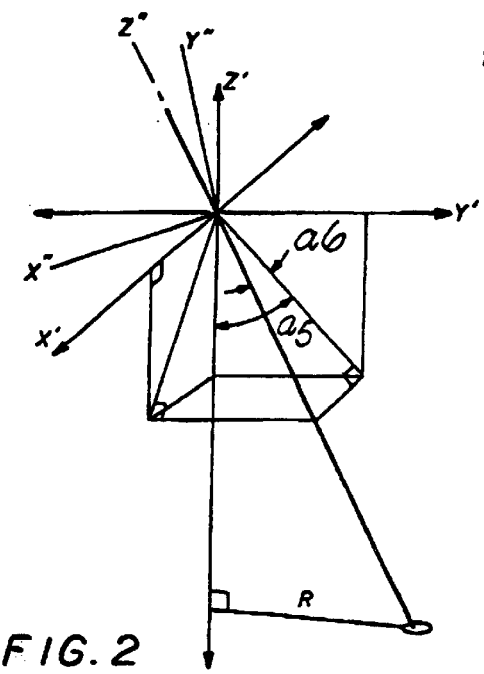
FIG. 2 is a schematic of an endoscope within two separate coordinate systems.

The linkage arm assembly 26 includes a first linkage arm 28 attached to a first rotary actuator 30 and an end effector 32. The first rotary actuator 30 is adapted to rotate the first linkage arm 28 and end effector 32 in a plane perpendicular to the z axis (x-y plane) The first rotary actuator 30 is connected to a second rotary actuator 34 by a second linkage arm 36. The second actuator 34 is adapted to rotate the first actuator 30 in the x-y plane. The second rotary actuator 34 is connected to the output shaft of the linear actuator 24. The actuators 24, 30 and 34 rotate in response to output signals provided by the computer 20. As shown in FIG. 2, the junction of the endoscope 16 and the end effector 32 define a second coordinate system which has an x' axis, a y' axis and a z' axis. The junction of the end effector 32 and endoscope 18 also define the origin of a third coordinate system which has a x' axis, a p axis and a z" axis. The z" axis parallel with the longitudinal axis of the endoscope 16.

The arm assembly may have a pair of passive joints that allow the end effector to be rotated in the direction indicated by the arrows. The actuators 24, 30 and 34, and joints of the arm may each have position sensors (not shown) that are connected to the computer 20. The sensors provide positional feedback signals of each corresponding arm component.

The system has a microphone 40 that is connected to the computer 20. The system may also have a speaker 42 that is connected to the computer 20. The microphone 40 and speaker 42 may be mounted to a headset 44 that is worn by the user. Placing the microphone 40 in close proximity to the user reduces the amount of background noise provided to the computer and decreases the probability of an inadvertent input command.

Figure 3:
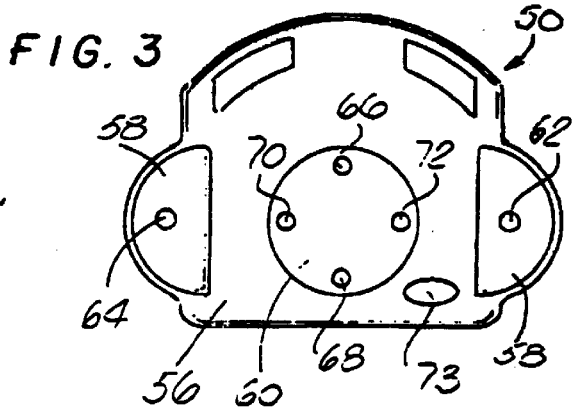
FIG. 3 is a top view of a foot pedal.

As shown in FIG. 3, the system may also have a foot pedal 50. The foot pedal 22 has a housing 56 that supports a pair of outer first foot switches 58 and a second foot switch 60. One outer foot switch 58 has a first pressure transducer 62 and the other switch has a second pressure transducer 64. The second foot switch 60 has third 66, fourth 68, fifth 70 and sixth 72 pressure transducers. The transducers are each connected to a corresponding operational amplifier that provides a voltage input to the computer 20. The pressure transducers 62–72 are preferably constructed so that the resistance of each transducer decreases as the surgeon increases the pressure on the foot switches. Such a transducer is sold by Interlink Electronics. The decreasing transducer resistance increases the input voltage provided to the computer 20 from the operational amplifier. Each transducer corresponds to a predetermined direction within the image displayed by the monitor. In the preferred embodiment, the first pressure transducer 62 corresponds to moving the endoscope toward the image viewed by the surgeon. The second transducer 64 moves the scope away from the image. The third 66 and fourth 68 transducers move the image "up" and "down", respectively, and the fifth 70 and sixth 72 transducers move the image "left" and "right", respectively. The pedal may have a button 73 that enables the foot pedal 50 and disable the voice command feature, or vice versa.

Figure 4:
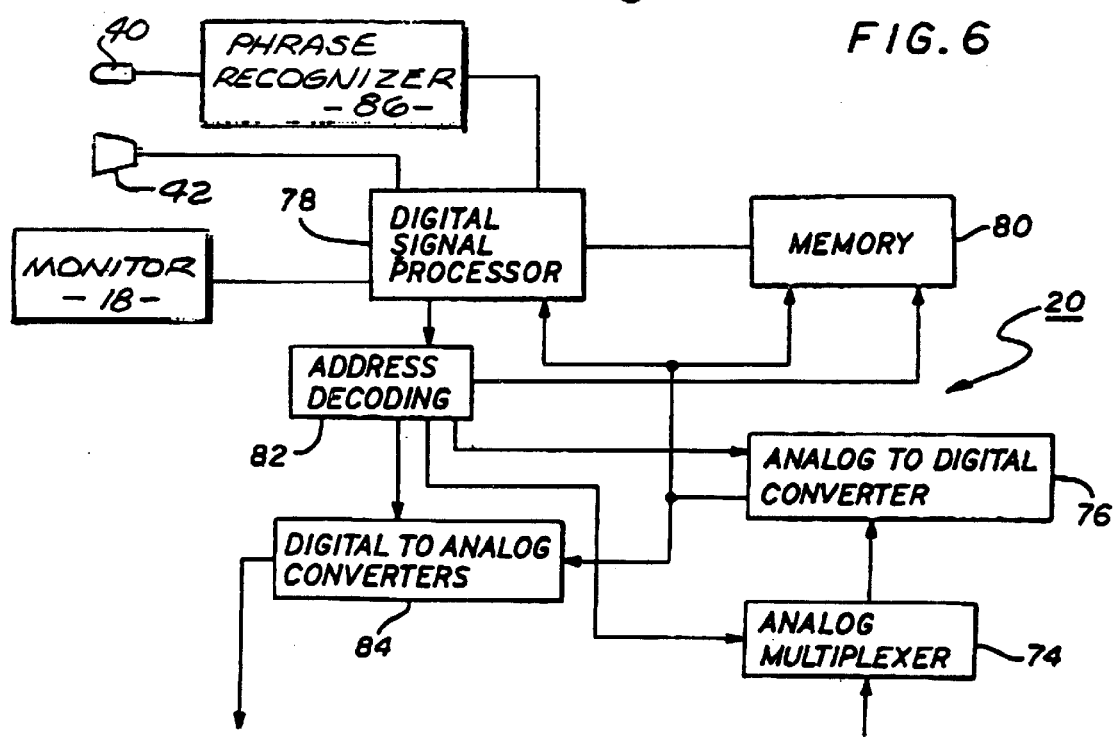
FIG. 4 is a schematic of a computer system.

FIG. 4 shows a schematic of the computer 20. The computer 20 has a multiplexer 74 which is connected to the pressure transducers of the foot pedal 50 and the position sensors of the arm. The multiplexer 74 is connected to a single analog to digital (A/D) converter 76. The computer 20 also has a processor 78 and memory 80.

The processor 78 is connected to an address decoder 82 and separate digital to analog (D/A) converters 84. Each D/A converter is connected to an actuator 24, 30 and 34. The D/A converters 84 provide analog output signals to the actuators in response to output signals received from the processor 78. The analog output signals have a sufficient voltage level to energize the electric motors and move the robotic arm assembly. The decoder 82 correlates the addresses provided by the processor with a corresponding D/A converter, so that the correct motor(s) is driven. The address decoder 82 also provides an address for the input data from the A/D converter 76 so that the data is associated with the correct input channel.

The computer 20 has a phrase recognizer 86 connected to the microphone 40 and the processor 78. The phrase recognizer 86 digitizes voice commands provided by the user through the microphone 40. The voice commands are then processed to convert the spoken words into electronic form. The electronic words are typically generated by matching the user's speech with words stored within the computer 20. In the preferred embodiment, the recognizer 86 is an electronic board with accompanying software that is marketed by Scott Instruments of Denton, Tex. under the trademark "Coretechs Technology".

The electronic words are provided to the processor 78. The processor 78 compares a word, or a combination of words to predefined robot commands that are stored within a library in the memory 80 of the computer 20. If a word, or combination of words match a word or combination of words in the library, the processor 78 provides output commands to the D/A converter 84 to move the robotic arm in accordance with the command.

Figure 5:
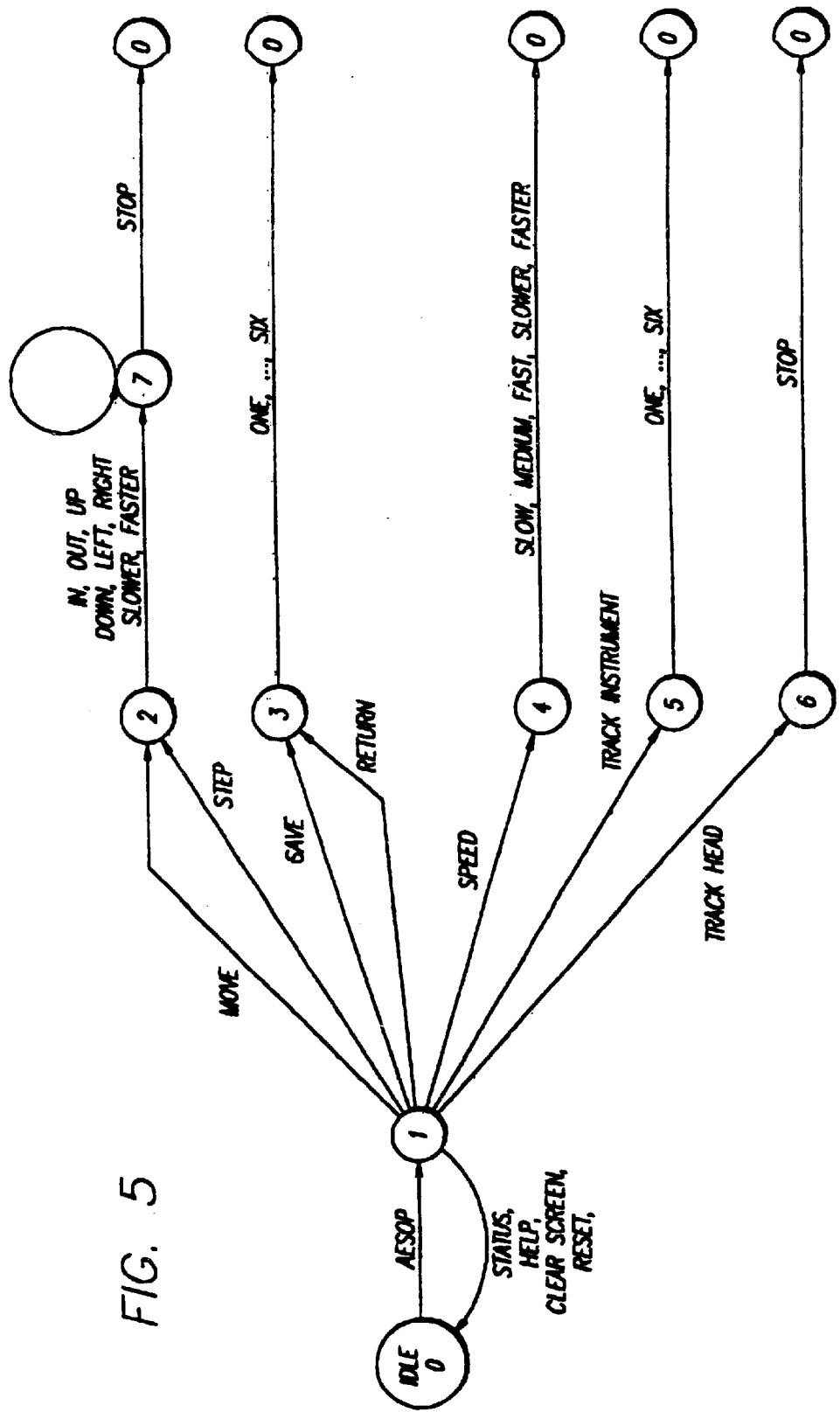
FIG. 5 is a schematic of a grammar process.

FIG. 5 shows exemplary words and combinations of words that provide robot commands. A grammar process is performed to determine whether the voice commands satisfy certain conditions. The process contains a number of states advanced by the satisfaction of a condition. If the voice command provided by the user satisfies a first condition, then the process proceeds to the first state. If a condition of a next state is satisfied then the process proceeds to the next corresponding state, and so forth and so on. For example, to prevent a robot command from being inadvertently spoken, it is desirable to predicate all voice commands with a qualifier. For example, the qualifier may be a name given to the robot such as "AESOP". Therefore when the user provides a voice command, the process initially determines whether the spoken word is AESOP. If the spoken word is not AESOP then the process ends. The term "stop" may be an exception to this rule, wherein the computer will stop arm movement when the user provides a simple "stop" voice command.

If the spoken word is AESOP the process continues to state 1. The process next determines whether the user has spoken a word that satisfies a condition to advance to states 2–6. These words include "move", "step", "save", "return", "speed", "track instrument" and "track head". The track instrument command is for a system which has the ability to move an endoscope to automatically track the movement of a second instrument that is inserted into the patient. The track head command may enable the system so that the endoscope movement tracks the user's eyes. For example, if the user looks to the right of the image displayed by the monitor, the robot will move the endoscope to move the image in a rightward direction. The move and step commands induce movement of the scope in a desired direction. The save command saves the position of the endoscope within the memory of the computer. The return command will return the scope to a saved position.

From states 2–6 the process will determine whether the user has spoken words that meet the next condition and so forth and so on. When a certain number of conditions have been met, the processor 78 will provide an output command to the D/A converter 84 in accordance with the voice commands. For example, if the user says "AESOP move left", the processor 78 will provide output commands to move the endoscope 12, so that the image displayed by the monitor moves in a leftward direction. The microphone 40 phrase recognizer 86 and grammar process essentially provide the same input function as the foot pedal 50, multiplexer 74 and A/D converter 76.

The processor 78 can also provide the user with feedback regarding the recognized command through the speaker 42 or the monitor 18. For example, when the user states "AESOP move right", after processing the speech, the processor 78 can provide an audio message through the speaker 42, or a visual message on the monitor 18, "AESOP move right". Additionally, the processor 78 can provide messages regarding system errors, or the present state of the system such as "speed is set for slow".

Figure 6:
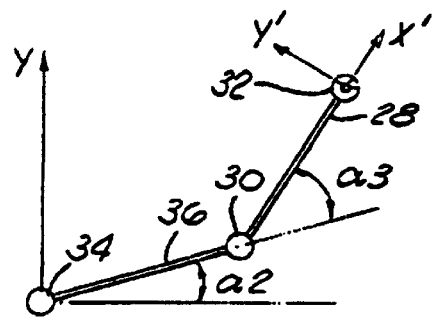
FIG. 6 is a schematic of a robotic arm.

Referring to FIG. 6, the processor 78 typically computes the movement of the robotic arm assembly 16 in accordance with the following equations.

$$a3 = \pi - \cos^{-1}\left(\frac{x^2 + y^2 - L1^2 + L2^2}{-2L1L2}\right) \quad (1)$$

$$\Delta = \cos^{-1}\left(\frac{x^2 + y^2 + L1^2 - L2^2}{2 \cdot L1\sqrt{x^2 + y^2}}\right)$$

$$a0 = \tan^{-1}2\left(\frac{y}{x}\right)$$

$$a2 = a0 + /-\Delta$$

where;
  a2=angle between the second linkage arm 36 and the x axis.
  a3=angle between the first linkage arm 28 and the longitudinal axis of the second linkage arm 36.
  L1=length of the second linkage arm.
  L2=length of the first linkage arm.
  x=x coordinate of the end effector in the first coordinate system.
  y=y coordinate of the end effector in the first coordinate system.

To move the end effector to a new location of the x-y plane the processor 78 computes the change in angles a2 and a3 and then provides output signals to move the actuators accordingly. The original angular position of the end effector is provided to the processor 78 by the position sensors. The processor moves the linkage arms an angle that corresponds to the difference between the new location and the original location of the end effector. A differential angle Δa2 corresponds to the amount of angular displacement provided by the second actuator 34, a differential angle Δa3 corresponds to the amount of angular displacement provided by the first actuator 30.

To improve the effectiveness of the system 10, the system is constructed so that the desired movement of the surgical instrument correlates to a direction relative to the image displayed by the monitor. Thus when the surgeon commands the scope to move up, the scope always appears to move in the up direction. To accomplish this result, the processor 78 converts the desired movement of the end of the endoscope in the third coordinate system to coordinates in the second coordinate system, and then converts the coordinates of the second coordinate system into the coordinates of the first coordinate system.

Referring to FIG. 2, the desired movement of the endoscope is converted from the third coordinate system to the second coordinate system by using the following transformation matrix;

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix} \quad (2)$$

where;

Δx"=the desired incremental movement of the scope along the x" axis of the third coordinate system.

Δy"=the desired incremental movement of the scope along the y" axis of the third coordinate system.

Δz"=the desired incremental movement of the scope along the z" axis of the third coordinate system.

a5=the angle between the z' axis and the scope in the y'-z' plane.

a6=the angle between the z' axis and the scope in the x'-z' plane.

Δx"=the computed incremental movement of the scope along the x' axis of the second coordinate system.

Δy"=the computed incremental movement of the scope along the y' axis of the second coordinate system.

Δz"=the computed incremental movement of the scope along the z' axis of the second coordinate system.

The angles a5 and a6 are provided by position sensors located on the end effector 32. The angles a5 and a6 are shown in FIG. 2.

The desired movement of the endoscope is converted from the second coordinate system to the first coordinate system by using the following transformation matrix;

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix} \quad (3)$$

where;

Δx'=the computed incremental movement of the scope along the x' axis of the second coordinate system.

Δy'=the computed incremental movement of the scope along the y' axis of the second coordinate system.

Δz'=the computed incremental movement of the scope along the z' axis of the second coordinate system.

π=is the angle between the first linkage arm and the x axis of the first coordinate system.

Δx=the computed incremental movement of the scope along the x axis of the first coordinate system.

Δy=the computed incremental movement of the scope along the y axis of the first coordinate system.

Δz=the computed incremental movement of the scope along the z axis of the first coordinate system.

The incremental movements Δx and Δy are inserted into the algorithms described above for computing the angular movements (Δa2 and Δa3) of the robotic arm assembly to determine the amount of rotation that is to be provided by each electric motor. The value Δz is used to determine the amount of linear movement provided by the linear actuator 24.

The surgical instrument is typically coupled to a camera and a viewing screen so that any spinning of the instrument about its own longitudinal axis will result in a corresponding rotation of the image on the viewing screen. Rotation of the instrument and viewing image may disorient the viewer. It is therefore desirable to maintain the orientation of the viewing image. In the preferred embodiment, the end effector has a worm gear (not shown) which rotates the surgical instrument about the longitudinal axis of the instrument. To insure proper orientation of the endoscope 16, the worm gear rotates the instrument 16 about its longitudinal axis an amount Δθ6 to insure that the y" axis is oriented in the most vertical direction within the fixed coordinate system. Δθ6 is computed from the following cross-products.

$$\Delta\theta 6 = zi'' \times (yo'' \times yi'')$$

where;

Δθ6=the angle that the instrument is to be rotated about the z" axis.

yo"=is the vector orientation of the y" axis when the instrument is in the first position.

yi"=is the vector orientation of the y" axis when the instrument is in the second position.

zi"=is the vector orientation of the z" axis when the instrument is in the second position.

The vectors of the yi" and zi" axis are computed with the following algorithms.

$$[zi''] = \begin{bmatrix} \cos a6 & 0 & -\sin a6 \\ -\sin a5 \sin a6 & \cos a5 & -\sin a5 \cos a6 \\ \cos a5 \sin a6 & \sin a5 & \cos a5 \cos a6 \end{bmatrix} \begin{bmatrix} 0 \\ 0 \\ 1 \end{bmatrix}$$

$$xi'' = z \times zi''$$

$$yl = zl \times xi$$

where;

a5=is the angle between the instrument and the z axis in the y-z plane.

a6=is the angle between the instrument and the z axis in the x-z plane.

z=is the unit vector of the z axis in the first coordinate system.

The angles a5 and a6 are provided by position sensors. The vector yo" is computed using the angles a5 and a6 of the instrument in the original or first position. For the computation of yi" the angles a5 and a6 of the second position are used in the transformation matrix. After each arm movement yo" is set to yi" and a new yi" vector and corresponding Δθ6 angle are computed and used to re-orient the endoscope. Using the above described algorithms, the worm gear continuously rotates the instrument about its longitudinal axis to insure that the pivotal movement of the endoscope does not cause a corresponding rotation of the viewing image.

The system may have a memory feature to store desired instrument positions within the patient. The memory feature may be enabled either by voice commands or through a button on an input device such as the foot pedal. When a save command is spoken, the coordinates of the end effector in the first coordinate system are saved in a dedicated address(es) of the computer memory. When a return command is spoken, the processor retrieves the data stored in memory and moves the end effector to the coordinates of the effector when the save command was enabled.

The memory feature allows the operator to store the coordinates of the end effector in a first position, move the end effector to a second position and then return to the first position with a simple command. By way of example, the surgeon may take a wide eye view of the patient from a predetermined location and store the coordinates of that location in memory. Subsequently, the surgeon may manipulate the endoscope to enter cavities, etc. which provide a more narrow view. The surgeon can rapidly move back to the wide eye view by merely stating "AESOP return to one".

In operation, the user provides spoken words to the microphone. The phrase recognizer 86 matches the user's speech with stored words and provides matched electronic words to the processor 78. The processor performs a grammar process to determine whether the spoken words are robot commands. If the words are commands, the computer energizes the actuators and moves the endoscope, accordingly. The system also allows the user to control the movement of the endoscope with a foot pedal if voice commands are not desired.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical robotic system for use in minimally invasive surgery, the minimally invasive surgery performed at an internal surgical site of a patient body, the surgical robotic system comprising:
    a surgical instrument having a proximal end and a distal end, the instrument extendible distally through an incision to the internal surgical site;
    a robot supporting the proximal end of the instrument, the robot moving the instrument in response to motor signals;
    a voice recognition system for inputting a plurality of spoken instructions, each spoken instruction including a spoken qualifier and a spoken direction of movement, the voice recognition system changing from a first state to a second state in response to the spoken qualifier and identifying the spoken direction of movement from among a plurality of alternative directions in the second state; and
    a computer coupling the voice recognition system to the robot, the computer generating the motor signals in response to the spoken instructions to move the distal end of the surgical instrument at the internal surgical site in the spoken directions by pivoting the instrument about the incision.

2. The surgical robotic system of claim 1, wherein the surgical instrument comprises an endoscope, and further comprising a monitor coupled to the endoscope for displaying an image of the internal surgical site.

3. The surgical robotic system of claim 2, wherein the distal end of the surgical instrument comprises a camera tip defining a camera coordinate frame, and wherein the computer calculates transformations between the camera coordinate frame and coordinate frames of the robot.

4. The surgical robotic system of claim 3, wherein the computer generates the motor signals using the transformations so that the camera tip moves in the internal surgical site to effect an instructed change in the image shown in the display.

5. The surgical robotic system of claim 3, wherein the camera tip defines a tip angle, and wherein the computer generates the motor signals using the transformations so that the camera tip moves in the internal surgical site to effect a change in zoom of the image shown in the display in response to a change in zoom instruction.

6. The surgical robotic system of claim 1, wherein the first surgical instrument is any of the following:
    a surgical tool;
    a forceps;
    a device positioned within the patient's body for transmitting an image outside of the patient's body;
    a laparoscope; and
    a medical telescope.

7. A minimally invasive surgical robotic method comprising: inserting a distal end of a surgical instrument through an incision to an internal surgical site;
    manipulating a proximal end of the instrument with a robot in response to motor signals; inputting spoken instructions, including a qualifier and a desired direction of movement, into a voice recognition system;
    changing a state of the voice recognition system from a first state to a second state in response to the qualifiers;
    selecting the desired direction of movement from a plurality of alternative directions of movement associated with the second state;
    generating the motor signals in response to the spoken instructions with a computer; and
    moving the distal end of the surgical instrument in the desired directions at the internal surgical site by pivoting the instrument about the incision with the robot in response to the motor signals.

8. The surgical robotic method of claim 7, further comprising displaying an image of the internal surgical site on a monitor.

9. The surgical robotic method of claim 8, wherein the surgical instrument comprises an endoscope, and further comprising inputting a change of image instruction and moving the endoscope with the robot so as to effect the instructed image change.

10. The surgical robotic method of claim 9, wherein the instructed image change comprises a change in zoom.

11. The surgical robotic method of claim 10, wherein the endoscope has a camera tip disposed at an angle relative to a shall of the camera.

12. The surgical robotic method of claim 7, wherein the distal end of the surgical instrument defines a distal coordinate reference frame, and further comprising calculating transformations between the distal coordinate frame and a coordinate frame of the robot with the computer and using the transformation to generate the motor signals.

13. A system for positioning a surgical instrument relative to a patient's body, comprising:
    a robotic manipulator having at least one controlled degree of freedom;
    a controller controlling the robotic manipulator;
    an instrument holder attaching a first surgical instrument to the robotic manipulator so that the first surgical instrument can pivot about an aperture into the patient body; and a voice recognition system coupled to the controller, the voice recognition system permitting a surgeon to verbally command motions of the robotic manipulator, the instrument initiating pivoting about the aperture in response to the commands only when the commands are preceded by a verbal qualifier, the instrument motions halting when the command comprises a stop command without a verbal qualifier.

14. A system for positioning a surgical instrument relative to a patient's body, as in claim 13, wherein the voice recognition system further permits the surgeon to select commands or operating modes from menus.

15. A system for positioning a surgical instrument relative to a patient's body, as in claim 13, further comprising a speech synthesis system to provide the surgeon with voice messages containing information about the operation of the system.

16. A system for positioning a surgical instrument relative to a patient's body, as in claim 15, wherein the first surgical instrument is a surgical camera and the speech synthesis system provides a message to the surgeon stating information about the movement of the surgical camera.

17. A system for positioning a surgical instrument relative to a patient's body, as in claim 15, wherein the first surgical instrument is a surgical camera and the speech synthesis system provides a message to the surgeon stating information about the movement of the surgical camera effect a zoom operation of the surgical camera.

18. A surgical system for use in minimally invasive surgery performed at an internal surgical site of a patient body, the system comprising:
an endoscope having a proximal portion and a distal end, said endoscope extendable distally through an aperture in a body wall to the internal surgical site;
a display operatively coupled to said endoscope for allowing a surgeon to view an image of the internal surgical site, the image changing in response to signals;
a voice recognition system for inputting a plurality of spoken instructions, the spoken instructions each including a qualifier and a command selected from a plurality of commands so as to effect a desired change in the image, the voice recognition system changing from a first state to a second state in response to the qualifier and only accepting the plurality of command in the second state; and
a computer operatively coupling the voice recognition system to the endoscope, the computer generating the signals in response to the spoken instructions to effect the desired change to the image of the internal surgical site.

19. The surgical system of claim 18, wherein the computer generates said signals so as to effect an instructed change in zoom of the image shown in the display in response to a change in zoom instruction.

20. The surgical system of claim 18, wherein the voice recognition system comprises a microphone for detecting spoken instructions and a speaker for providing audible messages to a surgeon regarding operation of the system.

21. The system of claim 20, wherein said audible messages comprise audible feedback indicating successful receipt of said spoken instructions.

22. The system of claim 20, wherein said audible messages comprise synthesized voice messages.

23. A minimally invasive surgical method comprising:
inserting a distal end of an endoscope through an aperture in a body wall of a patient to an internal surgical site;
displaying an image of the internal surgical site for perception by a surgeon controlling said endoscope in response to signals;
inputting a plurality of spoken instructions into a voice recognition system, each instruction comprising a qualifier which changes a state of the voice recognition system and a subsequent command;
generating, with a computer, said motor signals in response to said spoken instructions; and
changing the image in response to the signals.

24. The method of claim 23, further comprising inputting a change of image instruction and moving the endoscope with a robotic arm so as to effect the instructed image change.

25. The method of claim 23, wherein the instructed image change comprises a change in zoom.

26. The method of claim 23, further comprising providing audible messages containing information about the robotic surgery.

27. The method of claim 26, wherein said audible messages comprise audible feedback indicating successful receipt of said spoken instruction.

28. The method of claim 26, wherein said audible messages comprise synthesized voice messages.

29. The method of claim 26, wherein said audible messages comprise audible feedback indicating undesired movement of the distal end of the surgical instrument.

30. A system for positioning an endoscopic surgical instrument relative to a surgical site within a patient's body, comprising:
a robotic manipulator having at least one controlled degree of freedom;
a controller that is adapted to be capable of controlling the robotic manipulator;
an instrument holder for coupling said surgical instrument to said robotic manipulator; and
a voice recognition command input system operatively coupled to the controller, the voice recognition system having a first state and a second state, the voice recognition system changing from the first state to the second state in response to a verbal qualifier, the voice recognition system permitting a surgeon to specify desired motion of the surgical instrument to the controller only when in the second state, such that the robotic manipulator moves said instrument to a position relative to the patient's body, as specified by the surgeon using the command input system, by pivoting the instrument about an aperture into the patient's body.

31. A surgical system for use in an operating room to control a surgical instrument, the surgical instrument having a control input accepting control signals, the system comprising:
a voice recognition system having a first state and a second state, the voice recognition system in the first state accepting a verbal qualifier and changing from the first state to the second state in response to the verbal qualifier, the voice recognition system in the second state accepting a verbal command and comparing the verbal command to a plurality of command alternatives associated with the second state so as to identify a matching command; and
a processor operatively coupling the voice recognition system to the device, the processor generating the control signals at least in part in response to the identification of the matching command.

32. The system of claim 31, wherein the voice recognition system also has a third state, the voice recognition system changing from the second state to the third state in response to the verbal command being identified as a matching command from among the plurality of command alternatives, the voice recognition system in the third state accepting another plurality of command alternatives associated with the third state, the other command alternatives of the third state being different than the command alternatives of the second state.

33. The system of claim 32, wherein the voice recognition system has a fourth state, the voice recognition system changing from the second state to the fourth state in response to another verbal command selected from among the plurality of command alternatives of the second state, the voice recognition system in the fourth state accepting a plurality of command alternatives associated with the fourth state.

* * * * *